(12) United States Patent
Bruggeman et al.

(10) Patent No.: US 8,729,051 B2
(45) Date of Patent: May 20, 2014

(54) TRI- AND TETRA-OLIGO-SACCHARIDES SUITABLE AS AGGLUTINATION AGENTS FOR ENTERIC PATHOGENS

(75) Inventors: Geert Bruggeman, Brugge (BE); Katrien Deschepper, De Pinte (BE)

(73) Assignee: Nutrition Sciences N.V./S.A., Drongen (BE)

( * ) Notice: Subject to any disclaimer, the term of this patent is extended or adjusted under 35 U.S.C. 154(b) by 786 days.

(21) Appl. No.: 12/302,763

(22) PCT Filed: May 29, 2007

(86) PCT No.: PCT/EP2007/055187
§ 371 (c)(1),
(2), (4) Date: Jan. 26, 2009

(87) PCT Pub. No.: WO2007/138047
PCT Pub. Date: Dec. 6, 2007

(65) Prior Publication Data
US 2009/0186852 A1     Jul. 23, 2009

(30) Foreign Application Priority Data

May 30, 2006   (EP) .................................... 06447074

(51) Int. Cl.
*A61K 31/702*     (2006.01)

(52) U.S. Cl.
USPC ........................................................ 514/61

(58) Field of Classification Search
CPC ................................ A61K 31/702; C07H 3/06
USPC ............................................. 514/61; 536/123
See application file for complete search history.

(56) References Cited

U.S. PATENT DOCUMENTS

| 5,939,397 | A | 8/1999 | Heerze et al. | |
|---|---|---|---|---|
| 6,069,137 | A | 5/2000 | Heerze et al. | |
| 2007/0248649 | A1 * | 10/2007 | Sawatzki et al. | ............. 424/439 |

FOREIGN PATENT DOCUMENTS

| DE | 198 36 339 | 2/2000 | | |
|---|---|---|---|---|
| EP | 0 307 523 | 3/1993 | | |
| JP | 06-205669 | 7/1994 | | |
| JP | 07-236429 | 9/1995 | | |
| JP | 2001-149041 | 6/2001 | | |
| JP | 2001-226409 | 8/2001 | | |
| JP | 2006-511497 | 2/2008 | | |
| WO | WO 89/03218 | 4/1989 | | |
| WO | WO 95/17103 | A1 * | 6/1995 | ............... A23K 1/14 |
| WO | WO 2004/052121 | 6/2004 | | |
| WO | WO 2004/074496 | 9/2004 | | |

OTHER PUBLICATIONS

Sawatzki et al., machine translation of DE19836339, originally published in German in Feb. 2000, 3 pages; obtained Apr. 7, 2011.*
"derivative", Merriam-Webster Online Dictionary; also available at http://www.merriam-webster.com/dictionary/derivative; last viewed Jul. 15, 2009.*
Sundu, B. et al., World's Poultry Science Journal, "Palm kernel meal in broiler diets: effect on chicken performance and health", Jun. 2006, vol. 62, No. 2, pp. 316-325.*
Zdunczyk, Z. et al., Archives of Animal Nutrition, "Performance and Caecal Adaptation of Turkeys to Diets without or with Antibiotic and with Different Levels of Mannan-Oligosaccharide", 2004, vol. 58, No. 5, pp. 367-378.*
Morrow, et al. "Human Milk Oligosaccharides are Associated with Protection Against Diarrhea in Breast-Fed Infants," *The Journal of Pediatrics*, vol. 145, No. 3, pp. 297-303, Sep. 1, 2004.
Kvistgaard, et al. "Inhibitory Effects of Human and Bovine Milk Constituents on Rotavirus Infections," *Journal of Dairy Science*, vol. 87, No. 12, pp. 4088-4096, Dec. 1, 2004.
Shoaf, et al. "Prebiotic Galactooligosaccharides Reduce Adherence of Enteropathogenic *Escherichia coli* to Tissue Culture Cells," *Infection and Immunity*, vol. 74, No. 12, pp. 6920-6928, Dec. 2006.
International Search Report dated May 5, 2008.
Lesage, et al. "Cell Wall Assembly in *Saccharomyces cerevisiae*," Microbiology and Molecular Biology Reviews, vol. 70, No. 2, pp. 317-343, Jun. 2006.

* cited by examiner

*Primary Examiner* — Layla Bland
*Assistant Examiner* — Bahar Craigo
(74) *Attorney, Agent, or Firm* — Knobbe, Martens, Olson & Bear LLP

(57) ABSTRACT

Compositions which include a homotrimer, heterotrimer, homotetramer, and/or heterotetramer of a component such as pentose, hexose, an L or D isomer of a pentose or hexose, a β-form of a pentose or hexose, oxidized derivatives and mixtures of such compounds are disclosed as agglutination agents. The disclosed compositions are useful for agglutination of enteric pathogens and may be used for selectively controlling and regulating the microbial ecosystem in the gastrointestinal tract of a subject.

10 Claims, 1 Drawing Sheet

TRI- AND TETRA-OLIGO-SACCHARIDES SUITABLE AS AGGLUTINATION AGENTS FOR ENTERIC PATHOGENS

CROSS-REFERENCE TO RELATED APPLICATIONS

This application is the U.S. National Phase under 35 U.S.C. §371 of International Application PCT/EP2007/055187, filed May 29, 2007, which claims priority to EP 06447074.3, filed May 30, 2006.

FIELD OF THE INVENTION

This invention relates to the use of tri- and tetra-oligo-saccharides or their extracts or their derivatives or mixtures thereof as agglutination agent for pathogens. In particular it relates to the use of tri- and tetra-oligo-saccharides or their extracts or their derivatives or mixtures thereof to improve the microbial ecosystem in the gastrointestinal tract of the animal by specific enumeration of enteric pathogens followed by specific excretion, in order to improve weight gain, to reduce feed conversion and to improve in this way the feed value and health and well-being of the animal.

BACKGROUND

In modern animal production systems, the equilibrium between the intestinal flora and host animal is a delicate one, and disturbance of this equilibrium (by e.g. bacterial infection) has a negative impact on the overall performance of the animals (Eckel, 1999). Knowledge about the problems of intestinal microbial infection in livestock opens the door to completely new ways of influencing the bio-regulatory processes through feed additives, reducing the frequency of diarrhea and even losses, by stabilising the intestinal flora. In the past, this infection problem was partially solved by supplying feeds containing antibiotics as growth promoter.

But today, 50 years since the discovery of the traditional antimicrobials (e.g. penicillin), a lot of bacteria are now resistant to one and, in many cases, to multiple antimicrobials (Guillot, 1989). This resistance is proving fatal for thousands of people each year and results in high medical and heavy economic costs (Barton, 1998). The problem of antimicrobial resistance is global, but is partially caused by the world-wide application of antimicrobials in animal nutrition, since addition of them to feed formulations resulted in better performance (decreased feed conversions and higher growth rates) (Dupont and Steele, 1987; Prescott, 1997) and since more than half of all antimicrobial use was associated with animal production (Aarestrup, 1999). For some countries, e.g. the European Union, this led already to a prohibition of all antimicrobials, usable as growth promoters in feed formulations (Muirhead, 1998; Ross, 1999).

The problem with most traditional antimicrobials and other growth promoters in use today is that they attack bacteria at the intracellular level (Guillot, 1989). That is, they inhibit key enzymes in the synthesis of compounds used to build up the cell. Whenever this approach is used, bacteria can develop mutations of the enzymes involved or can develop mechanisms to rapidly pump the antimicrobial out of the cell. Alternatively, they can develop enzymes, which directly degrade the antimicrobial (e.g. β-lactamase) (Neu et al., 1980; Chirica et al., 1998). By plasmid transfer (via microbial conjugation), resistance can be rapidly transferred from one microbial cell to another (expansion of resistance) (Finland, 1971; Hedges and Jacob, 1974; Thompson, 1986; Hamilton, 1994).

Since the world-wide negative response on the use of the traditional antimicrobials (as growth promoters) in animal feeds, research is performed to search for new types of (natural) antimicrobials or growth promoters (mainly with another mode of action) (Mazza, 1998). During research for alternative (natural) antimicrobials, attention is nowadays mainly focussed on the use of several (organic) acids (Eckel, 1997; Liang, 1997; Radecki et al., 1988), new active probiotics (Chiquette and Banchaar, 1998; Garriga et al., 1998; Tannock, 1999), prebiotics (Olsen, 1996; Bower et al., 1998; Brown et al., 1998; Iji and Tivey, 1998; Houdijk et al., 1999), some plant- (onions and garlic) and herb extracts (essential oils) (De Koning and Hongbiao, 1999; Nielsen, 1999).

Nowadays, different types of oligosaccharides are already used in different applications. In some of these applications, oligosaccharides are (covalently) linked to a support or carrier.

WO2006022542 claims the combined use of indigestible oligo-saccharides and digestible galactose saccharide for the manufacturing of a composition for use in a method for the treatment and/or prevention of respiratory tract infection and/or respiratory tract infection disease, said method comprising orally administering a composition to a mammal, said composition comprising a) a galactose containing indigestible oligo-saccharide containing at least two terminal saccharide units, wherein at least one terminal saccharide unit is selected from the group consisting of glucose and galactose; and at least one terminal saccharide is selected from the group consisting of galactose and fucose; and b) at least 5 wt. % digestible galactose saccharide based on total dry weight of the composition, said saccharide being selected from the group consisting of galactose and digestible galactose containing saccharide containing at least two terminal saccharide units, wherein at least one terminal saccharide unit is selected from the group consisting of glucose and galactose; and at least one terminal saccharide is selected from the group consisting of galactose and fucose. Dosage is 0.1 to 12 grams transgalactooligo-saccharides with a degree of polymerisation between 2 and 10 per 100 gram dry weight of the composition.

WO2004074496 relates to a process for the production of a novel oligo-saccharide, the process comprising combining a substrate with *Lactobacillus* α-galactosidase enzyme. The invention also relates to the oligo-saccharide itself and to compositions comprising it. The invention further relates to the use of the oligo-saccharide, as well as compositions comprising it, for increasing beneficial bacteria in the gastrointestinal tract of an animal. Said oligo-saccharide is composed of galactose and glucose.

JP2002226496 provides a method for obtaining an oligo-saccharide by hydrolyzing a polysaccharide without adding an acid and to obtain an anti-infectious disease agent containing the oligo-saccharide. Solution: A sulfated polysaccharide exemplified by fucoidan is hydrolysed by passing the sulfated polysaccharide through a H type cation exchange resin column containing a carboxy group and a sulfate group as exchange groups followed by heating to give the oligo-saccharide. The oligo-saccharide obtained by the method is mainly composed of fucose and exhibits activity as an anti-infectious disease agent against *Escherichia coli, Vibrio*, . . . , by a function of preventing pathogenic fungi from attaching to the intestinal tract.

CN1370784 describes the preparation process of chitinamine oligo-saccharide includes dissolution of chitinamine with acetic acid, enzyme adding reaction, addition of hydrochloric acid and final spray drying. It is characterized by the added enzyme comprising hemicellulase, cellulase and β-amylase and the pressure reduced evaporation during reaction. The process degrades chitinamine into chitinamine oligo-saccharidewith 2-12 chitinamines and average molecular weight of 1500. The chitinamine oligo-saccharide may be used in inhibiting tumor, preventing and treating hepatosis, improving intestinal tract function, preventing and treating senile diseases.

JP2002121138 states the production of a composition for the prophylaxis of intestinal tract infectious diseases capable of carrying out the prophylaxis of the infectious diseases caused by causative bacteria of the intestinal tract infectious diseases. Solution: This composition for the prophylaxis of the intestinal tract infectious diseases comprises one or more kinds selected from the group consisting of oligo-saccharides derived from hen's egg yolk, oligo-saccharide-bound proteins and oligo-saccharide-bound peptides. The composition is especially sialyloligo-saccharides, sialyloligo-saccharide proteins and sialyloligo-saccharide peptides. Furthermore, the composition has inhibitory actions on the adhesion of the causative bacteria of the intestinal tract infectious diseases to host cells.

U.S. Pat. No. 6,069,137 describes a method for the treatment of traveller's diarrhoea mediated by enterotoxigenic $E.$ $coli$ in a subject, which method comprises administering to a subject in need of such treatment an effective amount of a composition comprising an oligo-saccharide sequence selected from the group consisting of β-Gal(1-4).β-Glc, .β.Gal(1-3).β.GalNAc, β.GalNAc(1-4).β.Gal, β.Gal(1-3).β.Gal, β.Gal(1-3).β.GalNAc(1-4).β.Gal and α.NeuAc(2-3).β.Gal covalently attached to derivatized silica particles, wherein said oligo-saccharide sequence binds at least one serotype of enterotoxigenic $E.$ $coli$, and wherein said composition is capable of being eliminated from the gastrointestinal tract.

EP1018342 describes the use of an agent in the preparation of a medicament for the prevention or treatment of an enteric infection mediated by an SLT, wherein said agent is a pharmaceutically acceptable solid inert affinity support capable of being eliminated from the gastrointestinal tract, which support has an affinity ligand covalently attached thereto through a spacer arm, wherein said ligand is characterized as an oligo-saccharide containing the disaccharide subunit αGal(1-4).βGal which binds the SLT; with the proviso that the disaccharide is not part of a αGal(1-4)ssGal(1-4).βGlcNAc trisaccharide or a αGal(1-4)ssGal(1-4).βGlc trisaccharide.

U.S. Pat. No. 5,939,397 describes a method to treat cholera and electrolyte imbalance and diarrhoea caused by $V.$ $cholera$ infection in a subject, which method comprises administering to a subject in need of such treatment an effective amount of a composition comprising an oligo-saccharide sequence covalently attached to a pharmaceutically acceptable solid, inert support through a non-peptidyl compatible linker arm, wherein said oligo-saccharide sequence when so bound to said solid, inert support is capable of binding one or more serotypes of $V.$ $cholerae$, and wherein said composition is capable of being eliminated from the gastrointestinal tract. Said oligo-saccharide is a 1-3 oligo-saccharide.

An object of the present invention is to provide a more specific and more active range of oligosaccharides having improved effects on the microbial ecosystem in the gastrointestinal tract. More in particular, the invention aims to provide a specific range of oligosaccharides for selectively controlling and regulating the microbial ecosystem in the gastrointestinal tract of a subject in need thereof, by specific enumeration of enteric pathogens followed by specific excretion thereof. When applied as a (feed) composition to animals, it is believed that said activity surprisingly results in an effective (feed) composition resulting in a improved feed conversion ratio (being the weight feed consumed per kg body weight gain) and improved feed value, health and well-being of the animal.

SUMMARY

The current patent application improves the state of the art by among other things:
  other bioactive oligo-saccharide structures, comprising mainly pentose saccharides (such as ribose, arabinose, xylose and lyxose), hexose saccharides (such as allose, altrose, gulose, idose, talose and mannose), glucuronic acid, galacturonic acid or their derivatives and mixtures well defined and smaller range of degree of polymerisation (3-4)
  Lower inclusion rate
  No need for supporting carrier or linking arm
  Only agglutination activity against pathogenic germs The present invention relates to the use of trimers and tetramers of oligosaccharides (also named tri-(oligo-)saccha-rides and tetra-(oligo-)saccharides) or derivatives thereof as novel and innovative agents with growth promoting capacities.

In a first aspect, the invention relates to the use of a composition comprising a homotrimer, heterotrimer, homotetramer and/or heterotretramer of a component selected from the group comprising pentose, hexose, a L or D isomers thereof, a α or β form thereof, combinations thereof, an oxidised derivative thereof, or any mixtures thereof, as an agglutination agent for agglutinating enteric pathogens. The present invention provides for the use of a selected group of saccharide oligomers (oligosaccharides) or derivatives thereof. The present invention relates to the use of oligosaccharides or derivative thereof having a low oligomerisation degree, and even more in particular, to tri- and tetra-(oligo-) saccharides or derivatives thereof. Advantageously, the present saccharide oligomers will provide satisfying effects when as such. They do not need to be (covalently) linked to any type of carrier or support. Furthermore, another advantage is that the selected group of saccharide oligomers shows lower inclusion rates, and is active only against enteric pathogens.

Preferably the present composition is a solid or liquid feed composition for selectively controlling and regulating the microbial ecosystem in the gastrointestinal tract of a subject in need thereof, the method comprising feeding said subject with a composition as defined herein. The invention further provides a method for controlling diarrhoea in a subject in need thereof, the method comprising administering to said subject a composition as defined herein. Another aspect of the invention includes a method for improving weight gain and reducing the feed conversion ratio of an animal in need thereof, the method comprising administering to said animal a composition as defined herein.

The present invention is at least in part based on the observation that providing to the animal tri- and tetra-(oligo-)saccharides or extracts or derivatives thereof as feed additive, changes the microbial ecosystem in the gastrointestinal tract of the animal in the following specific way. The total amount of enteric pathogens are in a first stage surprisingly enumerated in the lumen of the gastrointestinal tract (=selective development of enteric pathogens within the gastrointestinal tract) by avoiding their adhesion to the gastrointestinal wall, and in a second stage, the enumerated enteric pathogens are very quickly excreted (preferably within two weeks following application of tri- and tetra-(oligo-)saccharides) from the gastrointestinal tract of the animal. Enteric pathogens can include pathogenic bacteria, fungi, yeast and viruses. By fast elimination of enteric pathogens from the gastrointestinal tract, in second instance, better performances, which are reflected in daily growth and feed conversion, of the animals are obtained. The growth promoting effect of tri- and tetra-(oligo-)saccharides is already clearly visible at elution level of the enriched enteric pathogen strains from the gastrointestinal tract of the animal.

DETAILED DESCRIPTION OF INVENTION

Figure 1:
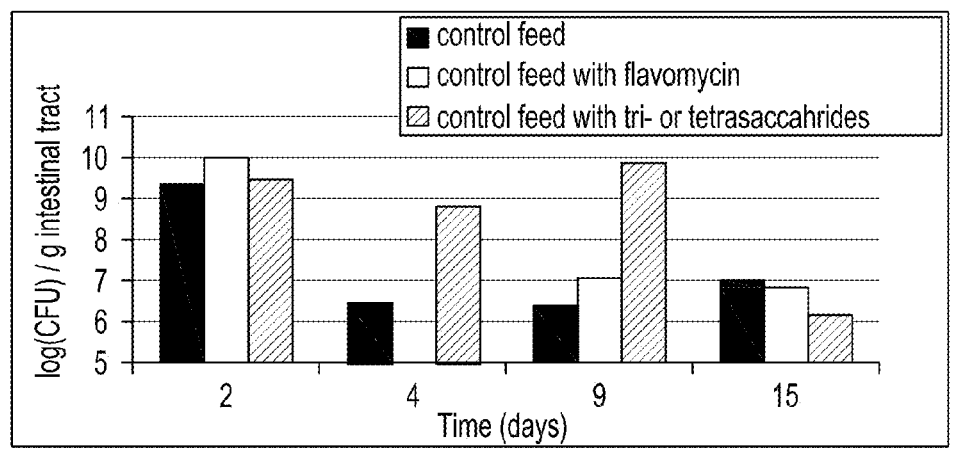
FIG. 1 illustrates the number of enteric pathogens in the gastrointestinal tract of chicken at different time points after feeding.

The present invention relates to a composition and the use thereof of as an agglutination agent for agglutinating enteric pathogens.

More in particular the present composition comprises oligosaccharide, and more preferably homotrimer, heterotrimer, homotetramer and/or heterotretramer of a component selected from the group comprising pentose, hexose, a L or D isomers thereof, a α or β form thereof, combinations thereof, a oxidised derivative thereof, or any mixtures thereof. The term oligosaccharide refers to a short chain of sugar molecules. The term "oligomers" is used herein to refer to compounds having more than one monomer unit. The oligomers present in the present composition substantially comprise trimer(s) and tetramer(s) of (oligo-)saccharide compounds, and more in particular homotrimers and/or heterotrimers.

A concentration up to about 1%, preferably an amount comprised between 0.01 and 0.2% by weight, eventually combined with other raw materials or other growth promoting substances, such as antibiotics, probiotics, prebiotics, acids, . . . , can be used to achieve this particular goal. 0.125 g/100 g feed has been found to be particularly suitable (see examples).

Conclusive, tri- and tetra-oligo-saccharides (or their extracts or their derivatives) cause in first instance growth of enteric pathogens (growth favouring of enteric pathogens) followed by washout of the enumerated enteric pathogens strains.

The novelty of the invention is that tri- and tetra-oligo-saccharides (or their extracts or their derivatives) are usable as a specific growth promoter in animal breeding, while the innovative characteristic of the invention is the enumeration of enteric pathogens in the gastrointestinal tract of the animal, prior to wash-out of the enumerated enteric pathogens. As a result, less diarrhoea and better performances are obtained. Moreover, since enteric pathogens are excreted from the animal, healthier animals are obtained. Animals can include birds (poultry, . . . ) and mammalians (pigs, ruminants, pets, . . . but also humans).

The observed effect is obtained during normal transit of the (eventually dried) tri- and tetra-oligo-saccharides (or an extract or a derivative) through the gastrointestinal tract of the animal.

The present invention relates to a method of using a composition or tri- and tetra-oligo-saccharides or their extracts or their derivatives or mixtures thereof as defined herein to improve the microbial ecosystem in the gastrointestinal tract of the animal by specific enumeration of previously adhered enteric pathogens prior to their specific excretion, in order to improve weight gain, to reduce feed conversion and to improve this way the feed value and health and well-being of the animal (causing e.g. less diarrhoea).

The present invention relates to a method of using a composition or tri- and/or tetra-oligo-saccharides or their extracts or their derivatives or mixtures thereof as defined herein as specific growth promoter in animal breeding.

The present invention relates to a method wherein tri- and/or tetra-oligo-saccharides are composed of pentose saccharides (such as ribose, arabinose, xylose and lyxose), hexose saccharides (such as allose, altrose, gulose, idose, talose and mannose), glucuronic acid, galacturonic acid or all their derivatives and combinations. This means also that the tri- or tetra-oligo-saccharides are homo- or hetero-oligomers.

The present invention relates to a method wherein hexoses are linked to each other by α or β bounds, or combination of both. The present invention relates to a method wherein galacturonic acids are linked to each other by α or β bounds, or combination of both. The present invention relates to a method wherein pentoses are linked to each other by α or β bounds, or combination of both.

The present invention relates to a method wherein the observed effect is obtained during normal transit and digestion process of the tri- and tetra-oligo-saccahrides or their extract or their derivative or a mixture thereof, through the gastrointestinal tract of the animal.

The present invention relates to a method wherein the tri- and/or tetra-oligo-saccharides or their extracts or their derivatives or mixtures thereof are used of up to about 1%.

The method according to the previous claims, wherein tri- and/or tetra-oligo-saccharides or their extracts or their derivatives or mixtures thereof either alone or in combination with other raw materials or other growth promoting substances, such as antibiotics, probiotics, prebiotics, acids, . . . are used.

The present invention relates to a method wherein tri- and/or tetra-oligo-saccharides or their extracts or their derivatives or mixtures thereof are dosed on dry basis at 0.125 g/100 g feed.

The present invention relates to a method wherein the enteric pathogens include the genera *Escherichia, Salmonella, Shigella, Klebsiella, Erwinia, Yersinia, Campylobacter, Helicobacter, Vibrio, Pseudomona* as well as other Gram negative bacteria.

The present invention relates to a method wherein enteric pathogens include the genera *Norovirus, Rotavirus*, as well as other viruses.

The present invention relates to a method wherein the animal is classified as bird (poultry, . . . ) or as mammalian (pig, ruminant, pet, . . . but also humans)

The present invention relates to a method wherein the oligo-saccharides are supplied to the animals in a solid or liquid phase.

In order that the present invention may be more clearly understood, the preferred form will be described with reference to the following examples.

EXAMPLES

Example 1

Influence of Tri- and Tetra-Manno-Oligo-Saccharides on the Microbial Ecosystem in the Gastrointestinal Tract of Poultry 3×40 one day old chickens were provided with following feeds: control feed, control feed supplemented with 3 ppm flavomycin and control feed supplemented with 0.025% tri- and/or tetra-manno-oligo-saccharides. The control feed was a mash feed, composed of raw materials suitable for animal nutrition. Water and feed were supplied ad libitum. The chickens were contaminated at day 2 with caecum contents of 3 week old chickens (most critical period for gastrointestinal problems). At regular time intervals, chickens were dissected and the enteric pathogen contents in the small intestine were determined by plate counting on MacConkey agar. FIG. 1 summarises the results.

From FIG. 1, it is clear that tri- and/or tetra-manno-oligo-saccharides has during the first week a positive effect on enteric bacteria growth/survival. Only after one week, the enteric bacteria content in the intestinal tract lowers very quickly, even to a level lower then the control and flavomycin treatment.

Example 2

Influence of Tri- and/or Tetra-Galacturonic-Oligo-Saccharides on Chicken Performance The same experimental conditions were applied as described in experiment 1. In this example, daily growth and feed conversion were monitored after 13 days. The results are summarised in table 1.

TABLE 1

Influence of tetra-oligo-saccharides on chicken performance

|  | Control | Control + flavomycin | Control + tetra-oligo-saccharides |
|---|---|---|---|
| Weight/chicken at day 1 | 43.1 | 43.54 | 43.66 |
| Weight/chicken at day 13 | 164.1 | 208.8 | 211.5 |
| Feed conversion/chicken | 1.80 | 1.51 | 1.48 |

From table 1, it can be concluded that use of tri- and/or tetra-galacturonic-oligo-saccharides in this particular test gave similar results as those obtained with a traditional growth promoter (flavomycin). Nevertheless, the mode of action is not comparable (see example 1)

Example 3

Influence of Tri- and/or Tetra-Galacturonic-Oligo-Saccharides on Piglet Performance At the start of the trial, 5 piglets were housed per pen. For each pen, one feeder (ad libitum) was installed for solid pelleted feed. One drinking nipple was installed per pen. The temperature at start was at 28° C. until 10 days after weaning. Afterwards, temperature was decreases to 25° C. Commercial non-medicated diets were given. Non-medicated means that the piglet doesn't receive any therapeutic antibiotics before and during the trial. The diets were given in the form of pellet.
The diets were the following:
Co: Control diet
Tr: Control diet+0.125% manno-oligo-saccharides
Design of the trial was as follows: 2 treatments (Co and Tr)×16 replicates×5 piglets At the start of the trial, the piglets (about 7 kg body weight) were allocated to the different pens by weight. This allocation was made in order to have an equal average weight and an equal standard deviation of the average weight for each treatment and pen. At regular time intervals, the piglets were weighed and feed consumption was monitored. This resulted in a daily growth, daily feed intake and feed conversion ratio (table 2).

TABLE 2

Zootechnical performance of piglets receiving manno-oligo-saccharides

| Feed | Parameter | Weaning | Growth | Total |
|---|---|---|---|---|
| Co | Daily growth (g/pig/d) | 116.0 | 320.9 | 218.4 |
|  | Feed intake (g/pig/d) | 156.3 | 419.5 | 287.9 |
|  | Feed conversion ratio | 1.73 | 1.63 | 1.65 |
| Tr | Daily growth (g/pig/d) | 131.9 | 322.2 | 224.8 |
|  | Feed intake (g/pig/d) | 225.2 | 515.1 | 363.7 |
|  | Feed conversion ratio | 1.73 | 1.68 | 1.65 |

From table 2, it can be concluded that zootechnical parameters of the piglets improve by supplying them manno-oligo-saccharides.

Example 4

Figure 2A:
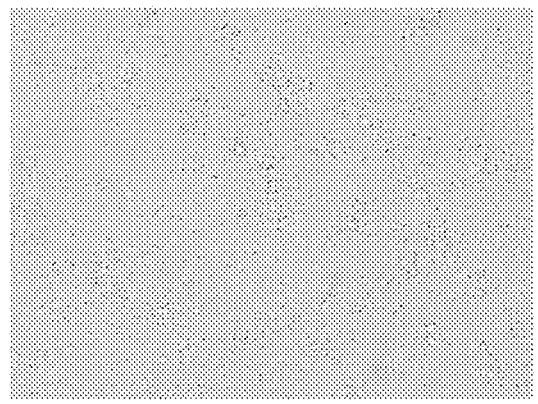
FIG. 2 illustrates the results of an agglutination assay using tri and/or tetra-mannosaccharides on A) *E. coli* K88 and B) *Lactobacillus amylovorus*
Figure 2B:
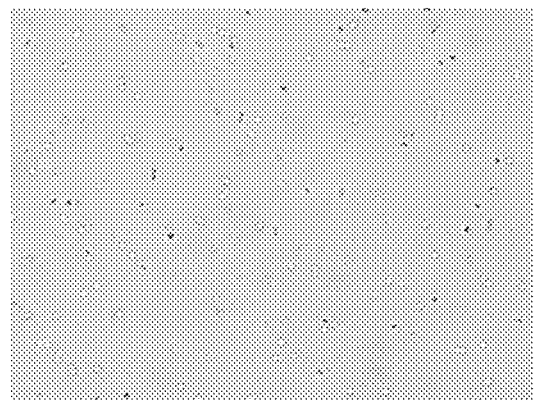

Influence of Tri- and/or Tetra-Manno-Oligo-Saccharides on Pathogen Agglutination Tri and/or tetra-manno-oligo-saccharides were incubated in liquid at a dose of 0.025% at pH 7.0 with *E. coli* K88 and *Lactobacillus amylovorus* cells for 10 minutes. After 10 minutes, agglutination was visualised by means of microscopic analysis. FIG. 2 shows the result. From FIG. 2, it is clear that tri and/or tetra-manno-oligo-saccharides are able to agglutinate *E. coli* K88 cells and not *Lactobacillus amylovorus* cells. This means that pathogenic germs are agglutinated by tri and/or tetra-manno-oligo-saccharides.

Example 5

Influence of Degree of Polymerisation of Xylo-Oligo-Saccharides on Pathogen Agglutination Xylose, tri-xylo-oligo-saccharides, tetra-xylo-oligo-saccharides, penta-xylo-oligo-saccharides en deca-xylo-oligo-saccharides were incubated at a dose of 0.025% at pH 7.0 with *E. coli* K88 and *Lactobacillus amylovorus* cells for 10 minutes. After 10 minutes, agglutination was visualised by means of microscopic analysis. It was clear best agglutination was obtained with tri-xylo-oligo-saccharides and tetra-xylo-oligo-saccharides. This means that pathogenic germs are preferably agglutinated by tri and/or tetra-xylo-oligo-saccharides.

REFERENCES

AARESTRUP, F. M. (1999). Association between the consumption of antimicrobial agents in animal husbandry and the occurrence of resistant bacteria among food animals. International Journal of Antimicrobial Agents, 12, 279-285.
BARTON, M. D. (1998). Does the use of antibiotics in animals affect human health. Aust. Vet. J., 76, 177-180.
BOWER, C. K., DAESCHEL, M. A. AND MCGUIRE, J. (1998). Protein antimicrobial barriers to bacterial adhesion. J. Dairy Sci., 81, 2771-2778.

BROWN, I. L., WANG, X., TOPPING, D. L., PLAYNE, M. J. AND CONWAY, P. L. (1998). High amylose maize starch as a versatile prebiotic for use with probiotic bacteria. Food, 50, 603-610.

CHIQUETTE, J. AND BANCHAAR, C. (1998). Effect of diet and probiotic addition on chemical composition of free and particle associated bacterial populations of the rumen. Can. J. Anim. Sci., 78, 115-120.

CHIRICA, L. C., GURAY, T., GURAKAN, G. C. AND BOZOGLU, T. F. (1998). Characterisation of extracellular β-lactamase from penicillin G-resistant cell of *Streptococcus thermophilus*. J. Food Prot., 61, 896-898.

DE KONING, W. AND HONGBIAO, D. (1999). Chinese herbs as feed additives. Feed Mix, 6(3), 17-18.

DUPONT, H. L. AND STEELE, J. H. (1987). Use of antimicrobial agents in animal feeds: implications for human health. Rev. Infect. Dis., 9, 447-460.

ECKEL, B. (1997). Feed acids in piglet feeding. Feed magazine, 1, 28-31.

ECKEL, B. (1999). Probiotics can improve intestinal microbe balance and feed hygiene. Feed Tech, 3(7), 39-41.

FINLAND, M. (1971). Changes in susceptibility of selected pathogenic bacteria to widely used antibiotics. Ann. NY Acad. Sci., 182, 5-20.

GARRIGA, M., PASCUAL, M., MONFORT, J. M. AND HUGAS, M. (1998). Selection of lactobacilli for chicken probiotic adjuncts. J. Appl. Microbiol., 84, 125-132.

GUILLOT, J. F. (1989). Apparition et évolution de la résistance bactérienne aux antibiotiques. Ann. Rech. Vét., 20, 3-16.

HAMILTON, J. O. C. (1994). Who will stop the mutant microbes. Business Week, August 1, 52-53.

HEDGES, R. W. AND JACOB, A. E. (1974). Transposition of ampicillin resistance from RP4 to other replicons. Mol. Gen. Genet., 132, 31-40.

HOUDIJK, J. G. M., BOSCH, M. W., TAMMINGA, S., VERSTEGEN, M. W. A., BERENPAS, E. B. AND KNOOP, H. (1999). Apparent Ileal and Total-Tract nutrient digestion by pigs as affected by dietary nondigestible oligo-saccharides. J. Anim. Sci., 77, 148-158.

IJI, P. A. AND TIVEY, D. R. (1998). Natural and synthetic oligo-saccharides in broiler chicken diets. World's Poultry Science Journal, 54, 129-143.

LIANG, C. (1997). Organic acids control harmful microorganisms in poultry feed. Zootehnica International, January, 36-39.

MAZZA, G. (ed.) (1998). Functional Foods. Technomic Publishing Company, Pennsylvania.

MUIRHEAD, S. (1998). EU ban of antibiotics draws sharp criticism. Feedstuffs, 70, 1-4.

NEU, C. H., , RICHMOND, M., MITSUHASHI, S., NORD, C. E., ROSS, G. W., KNOWLES, J. R. AND SUTHERLAND, R. (1980). β-lactamase: a major form of bacterial resistance. In: Current chemotherapy and infectious diseases. Springer Verlag, Berlin, 19-25.

NIELSEN, P. E. (1999). Denmark's approach to problem free feeding. Feed Mix, 6(5), 15-17.

OLSEN, R. (1996). Experience with mannanoligo-saccharides in commercial turkey production. Zootechnica International, August, 38-39.

PATENT WO/98126787. Prebiotics and probiotics.

PRESCOTT, J. F. (1997). Antibiotics: miracle drugs or pig food. Can. Vet. J., 38, 763-766.

RADECKI, S. V., JUHL, M. R. AND MILLER, E. R. (1988). Fumaric and citric acids as feed additives in starter pig diets: effect on performance and nutrient balance. J. Anim. Sci., 66, 2598-2605.

ROSS, I. W. (1999). Antibiotics in animal feed stocks and implications of the European Commission ban. Food Test Anal., 5, 8-10.

TANNOCK, G. W. (ed.) (1999). Probiotics: a critical review. Horizon Scientific Press, Wymondham.

THOMPSON, R. (1986). R plasmid transfer. J. Antimicrob. Chemother., 18, 13-23.

ZERIAL, A., SKERLAVAJ, B., GENNARO, R. AND ROMEO, D. (1987). Inactivation of herpes virus by protein components of bovine neutrophil granules. Antivir. Res., 7, 341-352.

What is claimed is:

1. A composition for agglutinating enteric pathogens, said composition comprising a homotrimer, heterotrimer, homotetramer and/or heterotetramer of a component selected from the group consisting of a β form of an aldopentose selected from the group consisting of arabinose and xylose; a β form of mannose, glucuronic acid, and galacturonic acid; combinations thereof; and any mixtures thereof, and optionally one or more additional components selected from the group consisting of antibiotics, probiotics, prebiotics, acids and combinations thereof, wherein said homotrimers, heterotrimers, homotetramers and/or heterotetramers are/is present in an amount from 0.01% to 0.2% by dry weight of the composition.

2. The composition according to claim 1, wherein said homotrimer, heterotrimer, homotetramer and/or heterotetramer are not covalently linked to a support or a carrier.

3. The composition according to claim 1, wherein said enteric pathogens are bacteria selected from the group consisting of the genera *Escherichia, Salmonella, Shigella, Klebsiella, Envinia, Yersinia, Campylobacter, Helicobacter, Vibrio,* and *Pseudomona*.

4. The composition according to claim 1, wherein said enteric pathogens are viruses selected from the group consisting of the genera *Norovirus,* and *Rotavirus*.

5. The composition according to claim 1 which is in a solid or liquid form.

6. The composition according to claim 1 which is a solid or liquid feed composition.

7. A feed composition, said composition comprising:
a homotrimer, heterotrimer, homotetramer and/or heterotetramer of a component selected from the group consisting of a β form of an aldopentose selected from the group consisting of arabinose, and xylose; a β form of mannose, glucuronic acid, and galacturonic acid; combinations thereof; and any mixtures thereof, and optionally one or more additional components selected from the group consisting of antibiotics, probiotics, prebiotics, acids and combinations thereof, wherein said homotrimers, heterotrimers, homotetramers and/or heterotetramers are/is present in an amount from 0.01% to 0.2% by dry weight of the composition, and a feed.

8. A method for controlling diarrhea in a subject in need thereof, the method comprising administering to said subject a composition according to claim 7.

9. A method for improving weight gain and reducing the feed conversion ratio of an animal in need thereof, the method comprising administering to said animal a composition according to claim 7.

10. A method for agglutinating enteric pathogens, said method comprising contacting one or more enteric pathogens with a composition according to claim 1.

* * * * *

UNITED STATES PATENT AND TRADEMARK OFFICE
CERTIFICATE OF CORRECTION

PATENT NO.        : 8,729,051 B2  
APPLICATION NO.   : 12/302763  
DATED             : May 20, 2014  
INVENTOR(S)       : Bruggeman et al.

Page 1 of 1

It is certified that error appears in the above-identified patent and that said Letters Patent is hereby corrected as shown below:

In the Claims

Column 10 at line 34, Claim 3, change "Envinia," to --Erwinia,--.

Signed and Sealed this
Eleventh Day of November, 2014

Michelle K. Lee
*Deputy Director of the United States Patent and Trademark Office*